US009102972B2

(12) United States Patent
Oh et al.

(10) Patent No.: US 9,102,972 B2
(45) Date of Patent: Aug. 11, 2015

(54) **MICROORGANISM *RHIZOBIUM* SP. KB10 HAVING PROPERTIES OF PROMOTING GROWTH OF *BOTRYOCOCCUS BRAUNII* AND INCREASING FATTY ACID CONTENT**

(71) Applicant: Korea Research Institute of Bioscience and Biotechnology, Daejeon (KR)

(72) Inventors: Hee Mock Oh, Daejeon (KR); Chi Yong Ahn, Daejeon (KR); Young Ki Lee, Daejeon (KR); So Ra Ko, Daejeon (KR); Hee Sik Kim, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 13/816,735

(22) PCT Filed: Jan. 11, 2013

(86) PCT No.: PCT/KR2013/000258
§ 371 (c)(1),
(2) Date: Feb. 13, 2013

(87) PCT Pub. No.: WO2013/133526
PCT Pub. Date: Sep. 12, 2013

(65) Prior Publication Data
US 2014/0087420 A1   Mar. 27, 2014

(30) Foreign Application Priority Data
Mar. 5, 2012  (KR) .................. 10-2012-0022346

(51) Int. Cl.
*C12P 39/00*   (2006.01)
*C10L 1/18*   (2006.01)
*C12N 1/12*   (2006.01)
*C12P 7/64*   (2006.01)
*C12R 1/41*   (2006.01)
*C12N 1/38*   (2006.01)
*C10L 1/02*   (2006.01)

(52) U.S. Cl.
CPC .................. *C12P 39/00* (2013.01); *C10L 1/026* (2013.01); *C10L 1/1802* (2013.01); *C12N 1/12* (2013.01); *C12N 1/38* (2013.01); *C12P 7/64* (2013.01); *C12P 7/6409* (2013.01); *C12P 7/6427* (2013.01); *C12R 1/41* (2013.01); *C10L 2200/0476* (2013.01); *C10L 2290/26* (2013.01); *Y02E 50/13* (2013.01)

(58) Field of Classification Search
CPC .............................. C12P 39/00; C10L 1/1802
USPC .................. 435/42, 70.1, 70.3, 347, 373
See application file for complete search history.

(56) References Cited

U.S. PATENT DOCUMENTS

2011/0275118 A1 *   11/2011   De Crecy ................. 435/42

FOREIGN PATENT DOCUMENTS

| KR | 10-2000-0000842 A | 1/2000 |
| KR | 10-2011-0002951 A | 1/2011 |
| KR | 10-2011-0007989 A | 1/2011 |
| WO | WO2008-119082 A2 | 10/2008 |

OTHER PUBLICATIONS

Rivas, Mariella O. et al., Interactions of *Botryococcus braunii* cultures with bacterial biofilms, Microbial ecology, May 26, 2010., vol. 60, No. 2, p. 628-635.
Li, Yan et al., Comparison of growth and lipid content in three *Botryococcus braunii* strains, Journal of Applied Phycology, Dec. 2005., 17: 551-556.
Rao, A.Ranga et al., Effect of salinity on growth of green alga *Botryococcus braunii* and its constituents, Bioresource Technology 98 (2007) 560-564.
International Search Report prepared by KIPO for PCT/KR2013/000258 (citing the above references listed in this IDS.).
International Preliminary Examination Report prepared by KIPO for PCT/KR2013/000258 (citing the above references listed in this IDS, and concluding that the claims of PCT/KR2013/000258 has novelty and inventive step.).
Chisti. Biotechnology Advances, 2007, vol. 25, p. 294-306.
Can. J. Biochem. Physiol. 1959, vol. 37, p. 911-917.

\* cited by examiner

*Primary Examiner* — Sharmila G. Landau
*Assistant Examiner* — Nghi Nguyen
(74) *Attorney, Agent, or Firm* — The PL Law Group, PLLC

(57) ABSTRACT

The present invention relates to *Rhizobium* sp. KB10 strain having properties of promoting growth of *Botryococcus braunii*, which is an alga capable of producing biodiesel, and also enhancing production performance of biodiesel. Mores specifically, it relates to novel *Rhizobium* sp. KB10 strain which has properties of promoting growth of *Botryococcus braunii* used for biodiesel production and also enhancing content of C18 (i.e., oleate) corresponding to high quality biodiesel component as much as 900%. By using root colonizing bacteria like *Rhizobium*, it is possible to promote effectively the slow cell growth of *Botryococcus braunii* and increase as much as possible the oleate amount, which is a high quality biodiesel component. Further, by carrying out mixture culture using such bacteria, problems associated with contamination by other microorganisms during a process of producing biodiesel by culture in an outside environment can be dramatically solved.

4 Claims, 3 Drawing Sheets

MICROORGANISM *RHIZOBIUM* SP. KB10 HAVING PROPERTIES OF PROMOTING GROWTH OF *BOTRYOCOCCUS BRAUNII* AND INCREASING FATTY ACID CONTENT

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2013/000258, filed Jan. 11, 2013, which claims priority to Korean Patent Application No. 10-2012-0022346, filed Mar. 5, 2012, entire contents of which are incorporated herein by reference.

BACKGROUND

1. Technical Field

The present invention relates to novel microorganism *Rhizobium* sp. KB10 having properties of promoting growth of *Botryococcus braunii* and increasing fatty acid content including oleate.

2. Description of the Related Art

Biodiesel from a raw material like plant oil like corn oil, rapeseed oil, and palm oil is a representative example of biodiesels that have been already commercially available and it is produced in rapidly increasing amount all over the world. However, due to the problems associated with high price of raw crops and relative cost increase caused by additional cost, or the like, its competitiveness is relatively weak compared to diesels derived from crude oil. In addition, recent price increase of raw crops poses new problem for competitiveness of the biodiesel. Examples of main supply source for biodiesel include phothosynthetic oil like plant oils and fats and algae oils. However, since the broader use of biodiesel having photosynthetic oils as a source may cause insufficient food supply or a new environmental problem relating to mass cultivation of raw crops, there has been a need for new supply source in another form.

Recently, as an energy source for stable and economically favorable production of biodiesel, algae are getting an attention. Algae are either photoautotrophs or photoheterotrophs and have a characteristic of growing in any place as long as solar energy, water, and carbon dioxide are available. They also have advantages that, compared to corn, palm, or sugar cane as a conventional plant raw material, the productivity is higher and also content of fats as a material for producing biodiesel is significantly higher than other supply sources. Algae can produce not only oils but also various useful substances, and they also have advantages as a renewable energy source as they are not conventional food crops. In case of microalgae belonging to algae, biodiesel production per unit area is about 58,700 L/ha, which is 130 times higher than soy bean (446 L/ha), when calculation is made for a standard case in which oil content is 30% (Chisti. Biotechnology Advances, 2007, vol. 25, p 294-306). Thus, it can be said that the mass culture of microalgae is a green technology which can prevent global warming by absorbing carbon dioxide present in atmospheric air and it enables biodiesel production from algae as seedlings.

Due to increasing focus from all over the world on production of biofuels by using algae, big national-level investments as well as related studies are being made. There is a representative international company like SOLIX, GreenFuel, Cyannotech, and the like. In Korea, the government leads many investments on basic research and industrialization.

Among microalgae, *Botryococcus braunii* is cluster type microalgae widely present in fresh water, salt lake, and warm climate or tropical regions. Cellular oil content is as high as 75%, which is much higher than other algae that are known so far, and the lipids produced by them can be easily transformed into biodiesel. However, the biggest problem in production of biodiesel using *Botryococcus braunii* is that the growth is slow (i.e., only two times in 6 days), and due to low growth rate, they can be easily contaminated with other microorganisms when they are cultured in large scale in outside environment.

Meanwhile, a method for producing fatty acid alkyl esters by using microorganism having oil-producing property is disclosed in Korean Patent Application Laid-Open No. 2011-0007989, a method for extracting hydrocarbons from microalgae is disclosed in Korean Patent Application Laid-Open No. 2000-0000842, and a method for producing hydroxyalkanoate alkyl ester by using microorganism having polyhydroxy alkanoate-producing property is disclosed in Korean Patent Application Laid-Open No. 2011-0002951. However, novel microorganism *Rhizobium* sp. KB10 having properties of promoting growth of *Botryococcus braunii* strain and increasing oleate content as disclosed in the present invention has not been described in any literatures at all.

SUMMARY

At least one embodiment of the present invention is devised in view of the problems described above.

Inventors of the present invention confirmed that, when co-cultured with *Rhizobium* sp. KB10, which is novel root colonizing bacteria isolated from an aqueous system, *Botryococcus braunii* exhibited not only the accelerated cell growth but also increased content of oleate as a biodiesel component with high quality, i.e., an increase by at least 9 times. Based on such findings, problem relating to slow cell growth, which is the biggest problem in biodiesel production using *Botryococcus braunii*, is solved and also content of various fatty acids including oleate is greatly increased in cultured *Botryococcus braunii*, and the present invention is completed accordingly.

In order to solve the problems described above, one or more embodiments of the present invention provides *Rhizobium* sp. KB10 which can promote growth of *Botryococcus braunii* strain.

Further, an embodiment of the present invention provides a method for promoting growth of *Botryococcus braunii* and a method for mass production of fatty acids including a step of co-culturing *Rhizobium* sp. KB10 strain and *Botryococcus braunii* strain.

Further, an embodiment of the present invention provides a microorganism formulation for mass production of fatty acids and a microorganism formulation for mass production of biodiesel, in which the formulation contains co-culture of *Rhizobium* sp. KB10 strain and *Botryococcus braunii* strain as an effective component.

Still further, an embodiment of the present invention provides a method for producing biodiesel including a step of producing fatty acids by co-culturing *Rhizobium* sp. KB10 strain and *Botryococcus braunii* strain.

The novel strain *Rhizobium* sp. KB10 according to an embodiment of the present invention not only can promote growth of *Botryococcus braunii* but also can increase effectively the content of oleate, which is a biodiesel component with high quality. Thus, by using the strain, contamination during large scale culture of *Botryococcus braunii* in an outside environment can be prevented, and a biodiesel component with high quality can be obtained in an amount increased by at least 900%. Therefore, it is believed that it has a huge effect on industrialization of biodiesel in terms of assuring obtainment of large amount of biomass, stable strain culture, cost saving according to an industrialization process, or the like.

DETAILED DESCRIPTION

Figure 1:
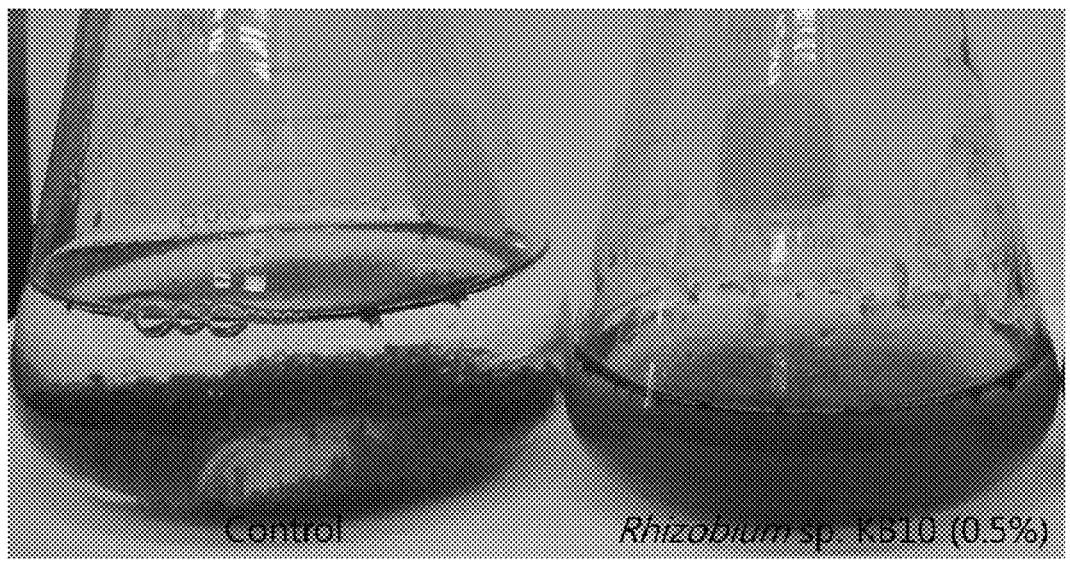
FIG. 1 illustrates a difference in cell growth of *Botryococcus braunii* when co-cultured with novel strain *Rhizobium* sp. KB10 (left: only *Botryococcus braunii* was cultured, right: novel strain *Rhizobium* sp. KB10 and *Botryococcus braunii* were co-cultured).

In order to achieve the purpose of the invention, the present invention provides *Rhizobium* sp. KB10 (*Rhizobium* sp. KB10) strain which can promote growth of *Botryococcus braunii* strain.

The novel strain of an embodiment of the present invention is obtained by a process including collecting top water and sediment from an aqueous system, isolating microorganisms using various nutrient media, and purifying it in pure form after three or four passages. Further, by treating culture solution of *Botryococcus braunii* with the purified microorganism isolate and a culture solution thereof, microorganisms which can promote the growth and increase content of oleate are finally selected. Among the strains that have been finally selected, microorganisms which promote growth of *Botryococcus braunii* were identified by a molecular biological method, i.e., an identification method based on 16s rDNA sequencing. As a result, it was identified as *Rhizobium* sp. and subsequently named *Rhizobium* sp. KB10. The novel strain, *Rhizobium* sp. KB10, was duly deposited with Korea Collection for Type Culture of Korean Research Institute of Bioscience and Biotechnology (having the address of KRIBB, Gwahak-ro-111, Yuseong-gu-Daejeon 305-808, Republic of Korea) under the Access number of KCTC 12131BP on Feb. 7, 2012. The deposit has been made under the terms of the Budapest Treaty and all restrictions imposed by the depositor on the availability to the public of the biological material will be irrevocably removed upon the granting of a patent.

Also provided by the present invention is a method for promoting growth of *Botryococcus braunii* including a step of co-culturing *Rhizobium* sp. KB10 strain and *Botryococcus braunii* strain.

When an excessive amount of *Rhizobium* sp. KB10 strain of an embodiment of the present invention is added for culturing of *Botryococcus braunii* strain, growth of the *Botryococcus braunii* strain may be inhibited. On the other hand, when *Rhizobium* sp. KB 10 strain is added in an extremely small amount, it may not have any effect on promoting growth of *Botryococcus braunii* strain. Thus, based on culture liquid of *Botryococcus braunii* strain, *Rhizobium* sp. KB10 strain is added in an amount of 0.1 to 10% (v/v) for co-culture. For example, *Rhizobium* sp. KB10 strain is added in an amount of 0.3 to 5% (v/v) for co-culture. Particularly, *Rhizobium* sp. KB10 strain may be added in an amount of 0.5% (v/v) for co-culture, but the amount is not limited to them.

As for the method for co-culturing the strains, any method known in the field may be used, and it is not limited to a particular method. For example, co-culturing of the strains may be performed for 30 days at 28° C., 120 μmol m$^{-2}$s$^{-1}$, but not limited thereto.

Also provided by the invention is a method for mass production of fatty acids including a step of co-culturing of *Rhizobium* sp. KB10 strain and *Botryococcus braunii* strain.

According to a method of one embodiment of the invention, the fatty acid is, for example, oleate, linolenate, linoleate, palmitate, or palmitoleate. Particularly, it may be oleate, but not limited thereto.

Also provided by the invention is a microorganism formulation for mass production of fatty acids, in which the formulation contains co-culture of *Rhizobium* sp. KB10 strain and *Botryococcus braunii* strain as an effective component.

According to a microorganism formulation of one embodiment of the invention, the fatty acid may be oleate, linolenate, linoleate, palmitate, or palmitoleate. Particularly, it may be oleate, but not limited thereto.

Also provided by the invention is a microorganism formulation for mass production of biodiesel, in which the formulation contains co-culture of *Rhizobium* sp. KB10 strain and *Botryococcus braunii* strain as an effective component.

The microorganism formulation for mass production of fatty acids or biodiesel according to an embodiment of the invention may be prepared by using co-culture of *Rhizobium* sp. KB10 strain and *Botryococcus braunii* strain as an effective component. The microorganism formulation for mass production of fatty acids or biodiesel according to an embodiment of the invention may be prepared as a solution, powder, or a suspension, but not limited thereto.

Also provide by the invention is a method for producing biodiesel including steps of producing fatty acids by co-culturing *Rhizobium* sp. KB 10 strain and *Botryococcus braunii* strain; and converting produced fatty acids into biodiesel.

As for the method for converting fatty acids produced by using the strain of the invention into biodiesel, any method well known in the field may be used, and it is not particularly limited to a specific method.

Herein below, the present invention is explained in greater detail in view of the Examples. However, it is evident that the following Examples are only given for exemplification of the present invention and by no means the present invention is limited to the following Examples.

EXAMPLES

Example 1

Isolation of Microorganisms

Surface water and sediments were collected from an aqueous system and subjected for 24 hour-culture at 37° C. by using various nutrient medium (LB, R2A, NA, 5× diluted LB: SERVA LB (Code 48502), Difco™ R2A (Item No. 218263), Difco™ NA (Item No. 213000)). As a result, various microorganisms were isolated first. The isolated microorganisms were purified to pure form by three or four passages using the same nutrient medium. After that, the culture medium containing Botryococcus braunii UTEX572 (The University of Texas at Austin, The culture collection of algae) was added with the purified algae and a culture medium, and then the microorganisms which increase the growth by 1.2 times or more were selected.

Example 2

Identification of Isolated Strain

For identification of the strain which has been isolated in the Example 1 above, culture was performed using the same medium and the genomic DNA was isolated by using a kit for isolating genomic DNA (Quiagen, Hilden, Germany). For PCR amplification of variable regions in 16S rDNA, two universal primers (9F, 536R) that are generally used for 16s rDNA were used; 9F primer: GAGTTTGATCCTGGCTCAG (SEQ ID NO: 1), and 536R primer: AAGGAGGTGATC-CAGCCGCA (SEQ ID NO: 2). PCR conditions are as follows: pre-denaturation at 95° C. for 5 min, and repeating 30 times the cycle consisting of denaturation at 95° C. for 1 min, annealing at 58° C. for 1 min, and extension at 72° C. for 1 min for DNA amplification. As a last step, extension at 72° C. was performed for 10 more minutes to terminate the PCR reaction. According to the result of electrophoresis, the amplified DNA with a size of 527 bp was isolated and then transfection was carried out by using a cloning vector pGEM T-EASY vector (Quiagen, Hilden, Germany). Sequence of the variable region in the resulting 16S rDNA with SEQ ID NO: 3 was subjected to comparative analysis using BLAST Search Program (NCBI). As a result, it was found that the novel strain of the present invention has high homology with Rhizobium (Table 1). Accordingly, the novel strain of the present invention was named as Rhizobium sp. KB10 and deposited with Korea Collection for Type Culture of Korean Research Institute of Bioscience and Biotechnology on Feb. 7, 2012 and given with Deposit Number of KCTC 12131BP.

TABLE 1

Result of nucleotide sequence analysis of 16S rDNA

| Strain | Homology (%) | Name of closely related microorganism | Accession No. |
|---|---|---|---|
| Rhizobium sp. KB10 | 1398/1407 (99.6) | Candidatus Rhizobium massiliae | AF531767 |

Example 3

Determination of Botryococcus braunii Growth Promotion and Oleate Production

The novel strain Rhizobium sp. KB10 was inoculated to R2A medium (Difco™ R2A (Item No. 218263)) and then cultured for 24 hours at 30° C. Ten % of the whole culture was then inoculated to the same but new medium and cultured for 16 hours under the same condition. By centrifuging for 20 min at 4000 rpm, the algae cells and the culture supernatant were separated from each other. The centrifuged algae cells were washed two times with sterilized and distilled water, and the cell number was adjusted by having OD600 nm=0.4. Botryococcus braunii UTEX572 was inoculated to 100 ml of BG11 medium ($NaNO_3$ 1.5 g, $K_2HPO_4$ 0.039 g, $MgSO_4.7H_2O$ 0.075 g, $Na_2CO_3$ 0.021 g, $CaCl_2$ 0.027 g, ferric citrate 0.006 g, citric acid 0.006 g, EDTA 0.001 g, Microelement stock solution 1 ml per Liter; microelement stock solution ($H_3BO_3$ 2.86 g, $MnCl_2.4H_2O$ 1.81 g, $ZnSO_4.7H_2O$ 0.222 g, $Na_2MoO_4.2H_2O$ 0.391 g, $CuSO_4.5H_2O$ 0.079, $Co(NO_3)_2.6H_2O$ 0.0494 g per 0.5 Liter)) followed by culture under the condition including 28° C. and 120 mmol m-2s-1. To 100 ml of culture liquid containing Botryococcus braunii UTEX572, algae cells of Rhizobium sp. KB10 which have been washed two times were inoculated in an amount of 0.5% or 5%, and then subjected to co-culture under the condition including 30 days at 28° C. and 120 μmol $m^{-2} s^{-1}$.

Figure 2:
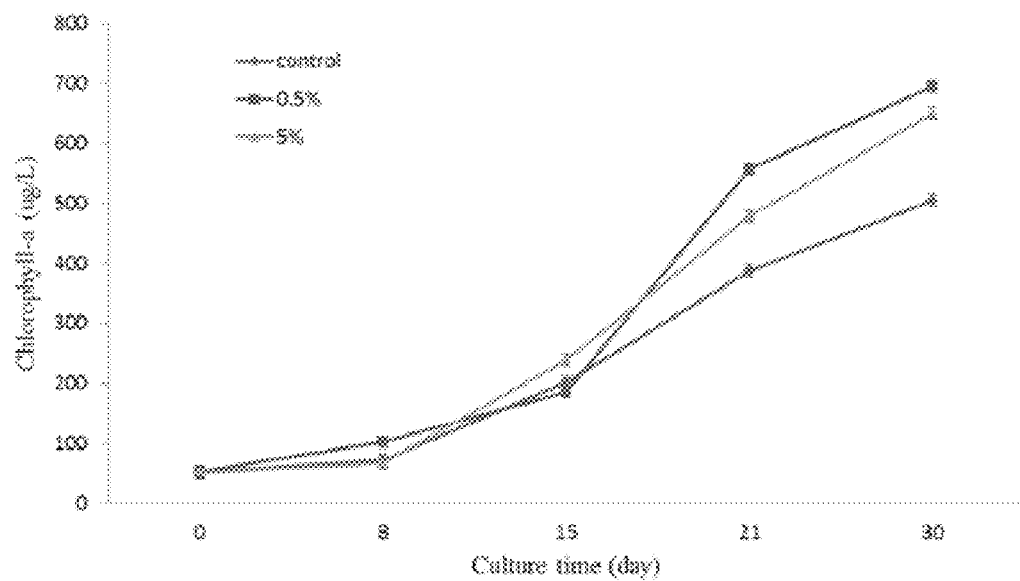
FIG. 2 is a graph for illustrating a difference in cell growth of *Botryococcus braunii* during co-culture according to various addition amount of the novel strain *Rhizobium* sp. KB10, in which the difference is expressed as the concentration of chlorophyll a (control: no addition of *Rhizobium* sp. KB10, 0.5%: addition of 0.5% *Rhizobium* sp. KB10, 5%: addition of 5% *Rhizobium* sp. KB10).

As shown in FIG. 1, growth of Botryococcus braunii UTEX572 was visually examined and compared between a single culture liquid to which the novel strain Rhizobium sp. KB10 is not inoculated and the co-culture liquid to which the novel strain is inoculated in an amount of 0.5%. As a result, it was confirmed that, excellent cell growth is obtained from the co-culture test group which has been treated with the novel strain Rhizobium sp. KB 10. In addition, concentration of chlorophyll a of Botryococcus braunii was examined and compared between a single culture liquid containing Botryococcus braunii only and the co-culture liquid to which Rhizobium sp. KB 10 is inoculated (FIG. 2). As a result, it was confirmed that the chlorophyll a is increased by 1.3 times or more in the co-culture test group. It was particularly found that the difference in cell growth has dramatically increased on Day 17 of the culture.

Figure 3:
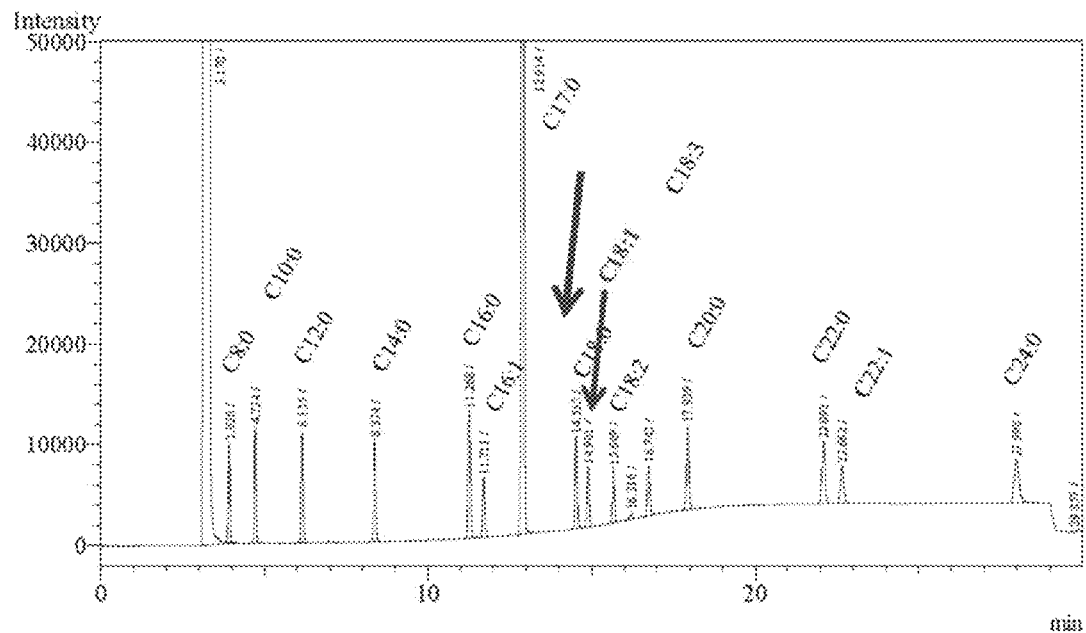
FIG. 3 shows the results illustrating the gas chromatography analysis profile of standard fatty acids.
Figure 4:
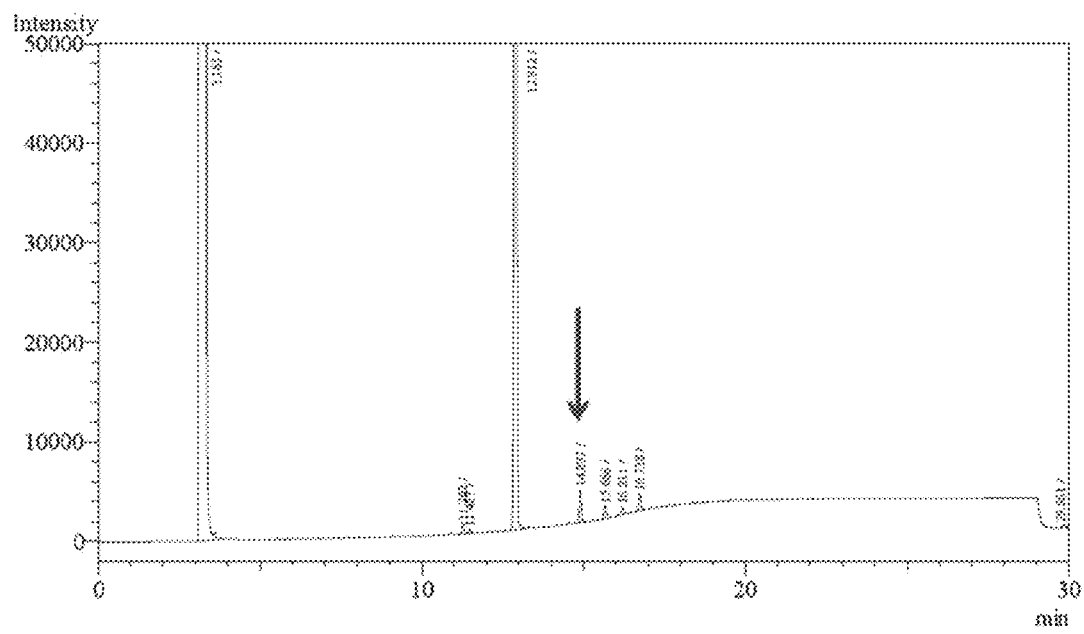
FIG. 4 shows the results obtained from the gas chromatography analysis of fatty acids that are obtained from *Botryococcus braunii* which has been cultured alone for 30 days.
Figure 5:
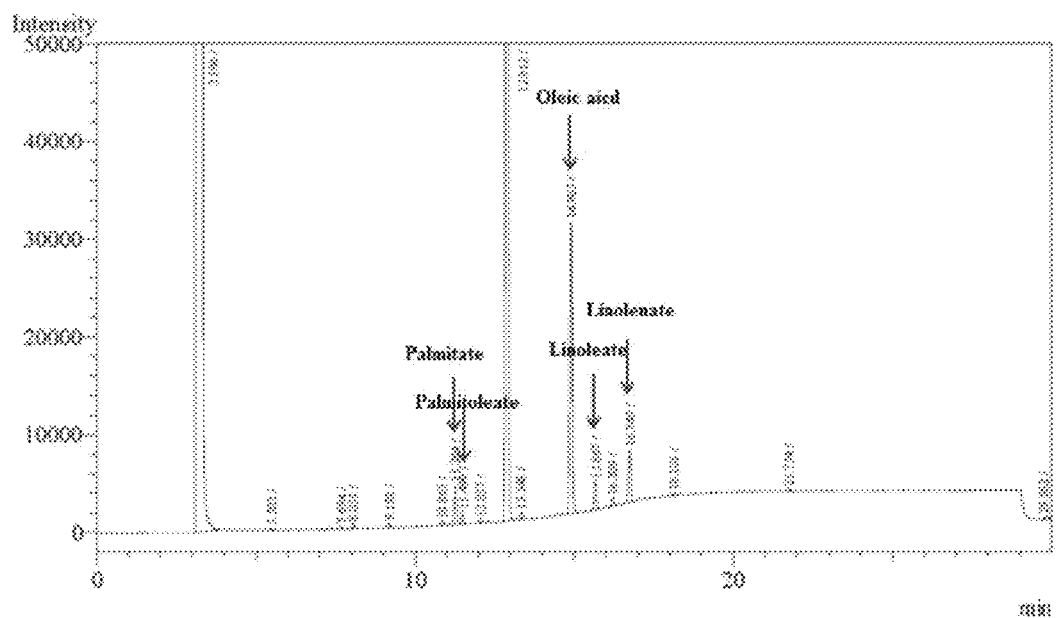
FIG. 5 shows the results obtained from the gas chromatography analysis of fatty acids that are obtained from *Botryococcus braunii* which has been co-cultured for 30 days with the novel strain *Rhizobium* sp. KB 10.
Figure 6:
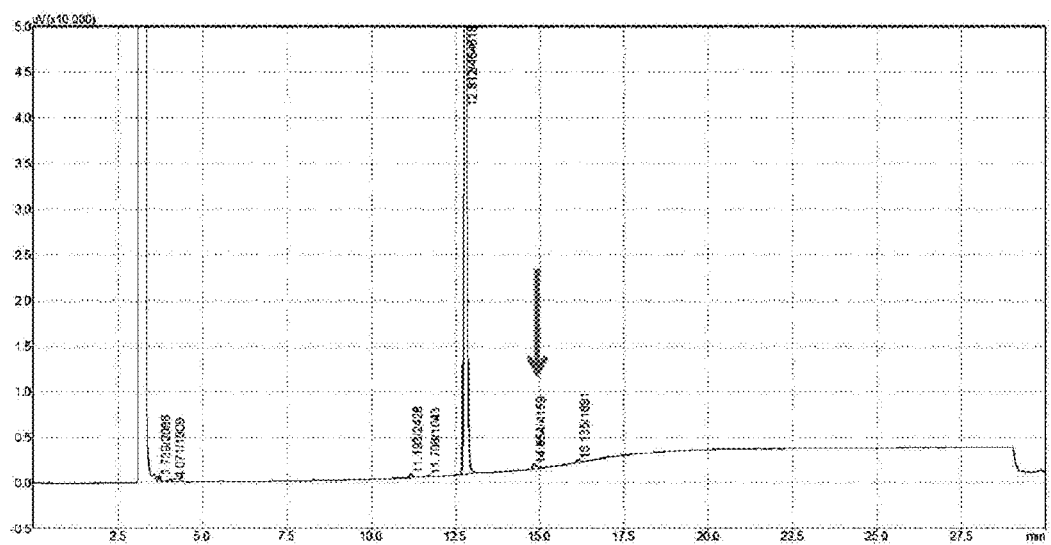
FIG. 6 shows the results obtained from the gas chromatography analysis of fatty acids that are obtained from the novel strain *Rhizobium* sp. KB 10 which has been cultured alone for 30 days.

Next, increase in oleate content was determined and compared between the culture liquid containing Botryococcus braunii only and the co-cultured test group, both cultured for 30 days. In order to compare the production amount of oleate by Botryococcus braunii, fatty acid standard materials that have been purchased from Sigma Aldrich were analyzed by gas chromatography as shown in FIG. 3. From the Botryococcus braunii test group and control group cultured for 30 days, fatty acids were extracted according to the method described by Bligh and Dyer (Can. J. Biochem. Physiol. 1959, vol. 37, p 911-917). The extracted fatty acids were then subjected to GC analysis under the same condition. As a result, it was found as shown in FIG. 5 that, oleate from the co-cultured Botryococcus braunii is increased by 9 times or more compared to the culture in which only Botryococcus braunii are cultured (FIG. 4). It was also found that linolenate, linoleate, palmitate, and palmitoleate were also dramatically increased (Table 2). To clearly determine the source of oleate that has been increased by co-culture, Rhizobium KB10 strain used for the co-culture was cultured for 30 days using R2A medium as a nutrient medium and then fatty acids therefrom were analyzed by gas chromatography (FIG. 6). As a result, it was found that the oleate content is extremely low in the novel strain Rhizobium KB 10 cultured for 30 days. In addition, the oleate was detected at extremely low level in a case in which culture is performed in the same medium for 24 hours (data are not presented).

TABLE 2

Results of fatty acid content analysis for culture liquid in which the
novel strain *Rhizobium* KB10 and *Botryococcus braunni*
are co-cultured (Peak area)

| Fatty acids | Control group | Test group |
| --- | --- | --- |
| Palmitate (C16:0) | 5042.7 | 18616.1 |
| Palmitoleate (C16:1) | 1705.0 | 5972.8 |
| Oleate (C18:1) | 15740.4 | 142421.8 |

TABLE 2-continued

Results of fatty acid content analysis for culture liquid in which the
novel strain *Rhizobium* KB10 and *Botryococcus braunni*
are co-cultured (Peak area)

| Fatty acids | Control group | Test group |
| --- | --- | --- |
| Linoleate (C18:2) | 6100.8 | 13887.0 |
| Linolenate (C18:3) | 8339.1 | 27339.0 |

The invention claimed is:

1. A method for promoting growth of *Botryococcus braunii*, the method comprising:
preparing a co-culture liquid by inoculating an isolated *Rhizobium* sp. KB10 strain deposited with Korean Collection for Type Cultures (KCTC) of Korea Research Institute of Bioscience and Biotechnology having the address of KRIBB, Gwahak-ro-111, Yuseong-gu-Daejeon 305-808, Republic of Korea under the Access number of KCTC 12131BP on Feb. 7, 2012 to *Botryococcus braunii* strain culture liquid, wherein, based on the culture liquid of said *Botryococcus braunii* strain, said isolated *Rhizobium* sp. KB10 strain is added in an amount of 0.1 to 10% (v/v); and
co-culturing said isolated *Rhizobium* sp. KB10 strain and said *Botryococcus braunii* strain.

2. A method for producing biodiesel, the method comprising:
preparing a co-culture liquid by inoculating an isolated *Rhizobium* sp. KB10 strain deposited with Korean Collection for Type Cultures (KCTC) of Korea Research Institute of Bioscience and Biotechnology having the address of KRIBB, Gwahak-ro-111, Yuseong-gu-Daejeon 305-808, Republic of Korea under the Access number of KCTC 12131BP on Feb. 7, 2012 to *Botryococcus braunii* strain culture liquid, wherein, based on the culture liquid of said *Botryococcus braunii* strain, said isolated *Rhizobium* sp. KB10 strain is added in an amount of 0.1 to 10% (v/v); and
producing fatty acids by co-culturing said isolated *Rhizobium* sp. KB10 strain and said *Botryococcus braunii* strain; and
converting produced fatty acids into biodiesel.

3. A method for producing fatty acid, the method comprising;
preparing a co-culture liquid by inoculating an isolated *Rhizobium* sp. KB10 strain deposited with Korean Collection for Type Cultures (KCTC) of Korea Research Institute of Bioscience and Biotechnology having the address of KRIBB, Gwahak-ro-111, Yuseong-gu-Daejeon 305-808, Republic of Korea under the Access number of KCTC 12131BP on Feb. 7, 2012 to *Botryococcus braunii* strain culture liquid, wherein, based on the culture liquid of said *Botryococcus braunii* strain, said isolated *Rhizobium* sp. KB10 strain is added in an amount of 0.1 to 10% (v/v); and
co-culturing said isolated *Rhizobium* sp. KB10 strain and said *Botryococcus braunii* strain.

4. The method for producing fatty acid according to claim 3, wherein the fatty acid is oleate, linolenate, linoleate, palmitate, palmitoleate, or a combination thereof.

\* \* \* \* \*

SEQUENCE LISTING

```
<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1
gagtttgatc ctggctcag                                                  19

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aaggaggtga tccagccgca                                                 20

<210> SEQ ID NO 3
<211> LENGTH: 1407
<212> TYPE: DNA
<213> ORGANISM: Rhizobium sp.

<400> SEQUENCE: 3
aacgaacgct ggcggcaggc ttaacacatg caagtcgaac gccccgcaag gggagtggca     60
gacgggtgag taacgcgtgg gaatctaccc atctctgcgg aatagctctg ggaaactgga    120
attaataccg catacgccct acggggggaaa gatttatcgg ggatggatga gcccgcgttg    180
gattagctag ttggtggggt aaaggcctac caaggcgacg atccatagct ggtctgagag    240
gatgatcagc cacattggga ctgagacacg gcccaaactc ctacgggagg cagcagtggg    300
gaatattgga caatgggcgc aagcctgatc cagccatgcc gcgtgagtga tgaaggcctt    360
agggttgtaa agctctttca ccgatgaaga taatgacggt agtcggagaa gaagccccgg    420
ctaacttcgt gccagcagcc gcggtaatac gaaggggggct agcgttgttc ggaattactg    480
ggcgtaaagc gcacgtaggc ggatatttaa gtcaggggtg aaatcccgca gctcaactgc    540
ggaactgcct ttgatactgg gtatcttgag tatggaagag gtaagtggaa ttccgagtgt    600
agaggtgaaa ttcgtagata ttcggaggaa caccagtggc gaaggcggct tactggtcca    660
ttactgacgc tgaggtgcga aagcgtgggg agcaaacagg attagatacc ctggtagtcc    720
acgccgtaaa cgatgaatgt tagccgtcgg gcagtatact gttcggtggc gcagctaacg    780
cattaaacat tccgcctggg gagtacggtc gcaagattaa aactcaaagg aattgacggg    840
ggcccgcaca agcggtggag catgtggttt aattcgaagc aacgcgcaga accttaccag    900
ctcttgacat cgggggtatg gcattggag acgatgtcct tcagttaggc tggccccaga    960
```

```
acaggtgctg catggctgtc gtcagctcgt gtcgtgagat gttgggttaa gtcccgcaac    1020
gagcgcaacc ctcgccctta gttgccagca tttagttggg cactctaagg ggactgccgg    1080
tgataagccg agaggaaggt ggggatgacg tcaagtcctc atggccctta cgggctgggc    1140
tacacacgtg ctacaatggt ggtgacagtg ggcagcgaga cagcgatgtc gagctaatct    1200
ccaaaagcca tctcagttcg gattgcactc tgcaactcga gtgcatgaag ttggaatcgc    1260
tagtaatcgc agatcagcat gctgcggtga atacgttccc gggccttgta cacaccgccc    1320
gtcacaccat gggagttggt tttacccgaa ggtagtgcgc taaccgcaag gaggcagcta    1380
accacggtag ggtcagcgac tggggtg                                        1407
```